(12) United States Patent  
Littell

(10) Patent No.: US 7,652,582 B2  
(45) Date of Patent: *Jan. 26, 2010

(54) SYSTEM AND METHOD FOR ERGONOMIC TRACKING FOR INDIVIDUAL PHYSICAL EXERTION

(76) Inventor: Stephanie Littell, 94 Reed St., Lexington, MA (US) 02421

( * ) Notice: Subject to any disclaimer, the term of this patent is extended or adjusted under 35 U.S.C. 154(b) by 98 days.

This patent is subject to a terminal disclaimer.

(21) Appl. No.: 11/986,309

(22) Filed: Nov. 20, 2007

(65) Prior Publication Data

US 2008/0136650 A1 Jun. 12, 2008

Related U.S. Application Data

(63) Continuation of application No. 11/143,834, filed on Jun. 2, 2005, now Pat. No. 7,315,249.

(60) Provisional application No. 60/576,726, filed on Jun. 3, 2004.

(51) Int. Cl.
*G08B 23/00* (2006.01)
*A61B 5/00* (2006.01)

(52) U.S. Cl. .............. 340/573.7; 340/573.1; 340/573.2; 340/686.1; 600/300; 600/301; 600/920

(58) Field of Classification Search ........................ None
See application file for complete search history.

(56) References Cited

U.S. PATENT DOCUMENTS

| | | | |
|---|---|---|---|
| 5,570,301 A * | 10/1996 | Barrus | 702/150 |
| 5,720,711 A | 2/1998 | Bond et al. | |
| 5,846,086 A | 12/1998 | Bizzi et al. | |
| 6,238,337 B1 * | 5/2001 | Kambhatla et al. | 600/300 |
| 6,249,590 B1 | 6/2001 | Young et al. | |
| 6,345,195 B1 | 2/2002 | Herskowits et al. | |
| 6,353,764 B1 * | 3/2002 | Imagawa et al. | 700/1 |
| 6,418,424 B1 | 7/2002 | Hoffberg et al. | |
| 6,625,303 B1 | 9/2003 | Young et al. | |
| 6,674,877 B1 | 1/2004 | Jojic et al. | |
| 2002/0015526 A1 | 2/2002 | Nomura et al. | |
| 2002/0118163 A1 | 8/2002 | Rozas | |
| 2003/0058111 A1 * | 3/2003 | Lee et al. | 340/573.1 |
| 2003/0058339 A1 | 3/2003 | Trajkovic et al. | |
| 2003/0059081 A1 | 3/2003 | Trajkovic | |
| 2003/0153817 A1 | 8/2003 | Knagenhjelm | |
| 2003/0181830 A1 | 9/2003 | Guimond et al. | |
| 2004/0077975 A1 | 4/2004 | Zimmerman | |
| 2004/0208496 A1 * | 10/2004 | Pilu | 396/263 |
| 2004/0230138 A1 * | 11/2004 | Inoue et al. | 600/595 |
| 2006/0211462 A1 * | 9/2006 | French et al. | 463/1 |

FOREIGN PATENT DOCUMENTS

CN 1460235 A 12/2003
JP 2003-070768 3/2003

* cited by examiner

*Primary Examiner*—Julie Lieu
(74) *Attorney, Agent, or Firm*—Hamilton, Brook, Smith & Reynolds, P.C.

(57) ABSTRACT

A system and method are provided for tracking a user's posture. The system and method include an environmental module for determining the user's physical environment, a biomechanical module for determining at least a user's posture in the user's physical environment, and an output module for outputting to the user an indication of at least the user's posture relative to at least a target correct posture. The physical environment can include a computer workstation environment, a manufacturing environment, a gaming environment, and/or a keypadding environment.

18 Claims, 5 Drawing Sheets

SYSTEM AND METHOD FOR ERGONOMIC TRACKING FOR INDIVIDUAL PHYSICAL EXERTION

RELATED APPLICATION

This application is a continuation of U.S. application Ser. No. 11/143,834, filed Jun. 2, 2005, which issued as U.S. Pat. No. 7,315,249 on Jan. 1, 2008, which claims the benefit of U.S. Provisional Application No. 60/576,726, filed on Jun. 3, 2004, the entire teachings of which are herein incorporated by reference.

BACKGROUND OF THE INVENTION

In ergonomics, physical exertion (e.g. work) is studied to try to reduce user fatigue and discomfort. As an individual exerts physical effort, physiological and biomechanical factors interweave. Physiologically, the human structures of ergonomic issue are skeletal and muscular. Individuals of differing shoulder breadth, for example, will position somewhat differently over a same-size keyboard. Biomechanically, components of ergonomic issue include posture, force, repetition and vibration. An upright sitting posture while manipulating a pointing device, for example, engenders different body exertion than a slouching posture.

Posture ranks right up at the top of the list when you are talking about good health. It is as important as eating right, exercising, getting a good night's sleep and avoiding potentially harmful substances like alcohol, drugs and tobacco. Good posture is a way of doing things with more energy, less stress and fatigue. Without good posture, a person's overall health and total efficiency may be compromised. Because the long-term effects of poor posture can affect bodily systems (such as digestion, elimination, breathing, muscles, joints and ligaments), a person who has poor posture may often be tired or unable to work efficiently or move properly.

Poor posture could bring on more severe musculoskeletal disorders (MSDs) such as ruptured disc or carpal tunnel syndrome. Excessive loading of the back musculoskeletal structures could weaken and even rupture a spinal disc. Carpal tunnel syndrome is normally caused by repetitive use of a hand or a wrist, where posture of the larger musculoskeletal structures (neck, arm) and/or finer structures (wrist, fingers) affects loading.

MSDs can happen to anyone who exerts repeated physical effort over periods of time. Stressful wrist, arm, neck and/or back positions, whether from working at a desk, long distance driving or lifting boxes, only aggravate the potential for damage.

SUMMARY OF THE INVENTION

The present invention provides a low cost non-invasive mechanism for preventing various kinds of incapacitating trauma that occur through incorrect ergonomic usage. The present invention uses real-time mirroring and positive modeling to address both prevention and intervention purposes.

A system and method are provided for tracking a user's posture. The system and method include an environmental module for determining the user's physical environment, a biomechanical module for determining at least a user's posture in the user's physical environment, and an output module for outputting to the user an indication of at least the user's posture relative to at least a target correct posture. The physical environment can include a computer workstation environment, a manufacturing environment, a gaming environment, and/or a keypadding environment.

In a preferred embodiment, the environmental module includes a scene module and a snapshot module, the scene and the snapshot modules capture a digital representation of a background of the user's physical environment. The biomechanical module includes an active scene module for capturing a digital representation of the user in the user's physical environment, and a runtime mirror module for processing the digital representation of the user in the user's physical environment. The output module includes a display for displaying to the user the user's posture relative to a target correct posture.

In one embodiment, the output module further includes an audio device for outputting to the user an audio indication of the user's posture relative to the target correct posture. The output can be displayed in a window of a multi-window environment. The representation of the user's posture can be superimposed with the target correct posture.

In one embodiment at least one digital camera can be used in determining the user's physical environment and/or in determining the user's posture.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Ergonomic factors are expressed with respect to an environment of physical exertion. That is, the particular expression of various ergonomic factors yields ergonomic metrics pertaining to a particular type of physical environment, e.g. clerical, manufacturing. The physical environment includes an individual (user) and a set of needed tools, e.g. computing keyboard, pointing device. Thus, the set of ergonomic metrics express the recommended position of the working individual with respect to his/her type of tools.

Figure 1:
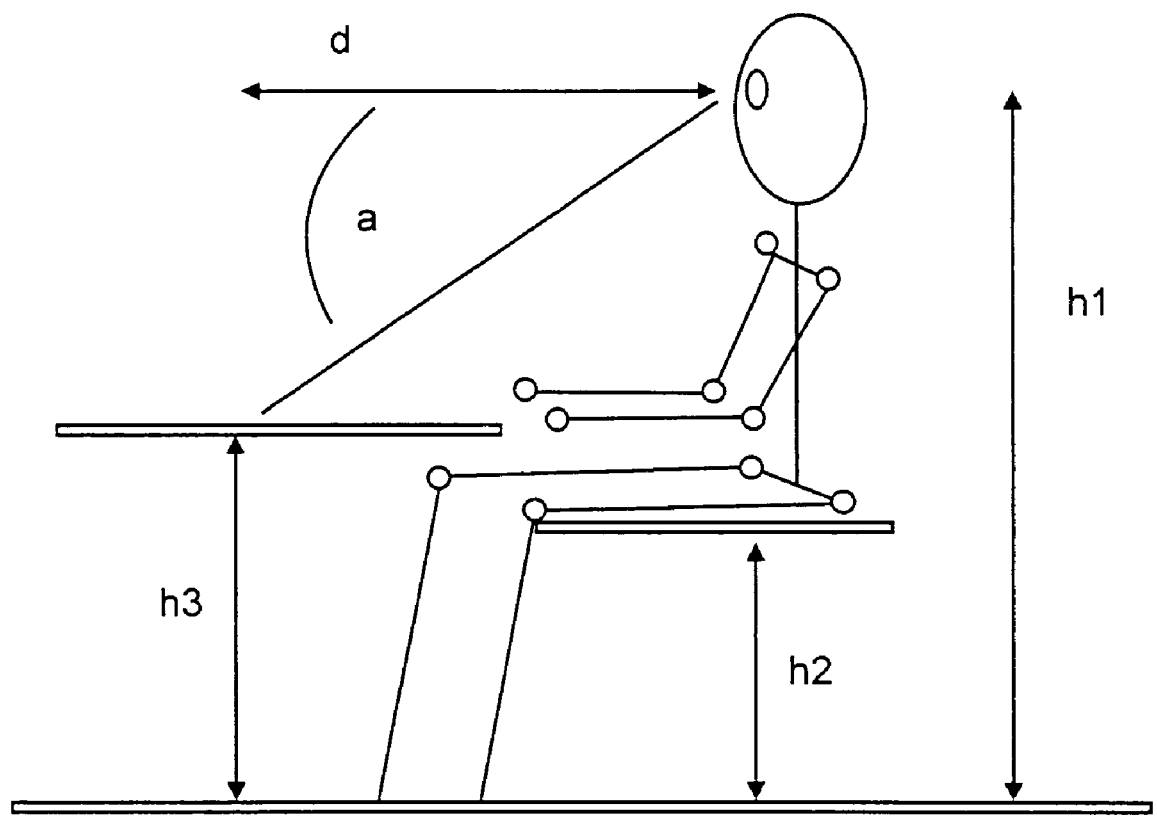
FIG. 1 illustrates a correct target posture and associated ergonomic metrics.

Target correct posture guidelines for computer workstation usage have been established by ANSI/HFS 100-1988 (ANSI) and BSR/HFES 100 Draft Standard, the entire teachings of which are herein incorporated by reference. FIG. 1 illustrates a correct target posture and associated ergonomic metrics as described in the aforementioned guidelines.

The published national guidelines include seat pan, work surface and screen viewing heights (h2, h3, and h1 respectively) to the nearest tenth-inch/centimeter (ANSI) or alternatively elbow, shoulder abduction and flexion, wrist flexion and extension, and torso-to-thigh angles (BSR) to the nearest degree. The guideline measurements, if complied with, dictate that the individual's posture must correspond to within a tenth-inch/centimeter or one angle degree with respect to posture segments or angles (such as distance "d" and angle "a" in FIG. 1).

An instrumentation approach has been used in specialized cases to provide a user ergonomic metrics based upon the user's work environment. To achieve sufficient accuracy, the instrumentation approach typically includes devices such as goniometers and/or height yardsticks, requiring physically-proximate equipment around or next to each computing user. When a user changes from a seated position to a standing position, or just reaches for a cup of coffee, the instrumentation approach to achieve accuracy would require repositioning all/some equipment in order to sample all measurements again. The aforementioned approach has not been practical to implement apart from controlled settings.

Another implementation of the instrumentation approach can incorporate wired or wireless body sensors attached at various points on the user's body. This approach would require such sensors to be attached daily, and to be unattached again when leaving the work environment. Again, the instrumentation approach has not been practical to implement apart from controlled settings.

Standard approaches today use written checklists or a one-time expert evaluation, so that an individual may try to internalize the 5-10 measurement metrics to continuously apply.

The present invention utilizes an alternative vision-based approach which requires no equipment physically around or next to each individual. The scope of user motion, such as seated/standing or reaching for coffee, would increase without requiring such repositioning as needed in the instrumentation approach. These user benefits could allow for more widescale adoption of ergonomic practices, by minimizing invasiveness and individual adoption cost.

Figure 2:
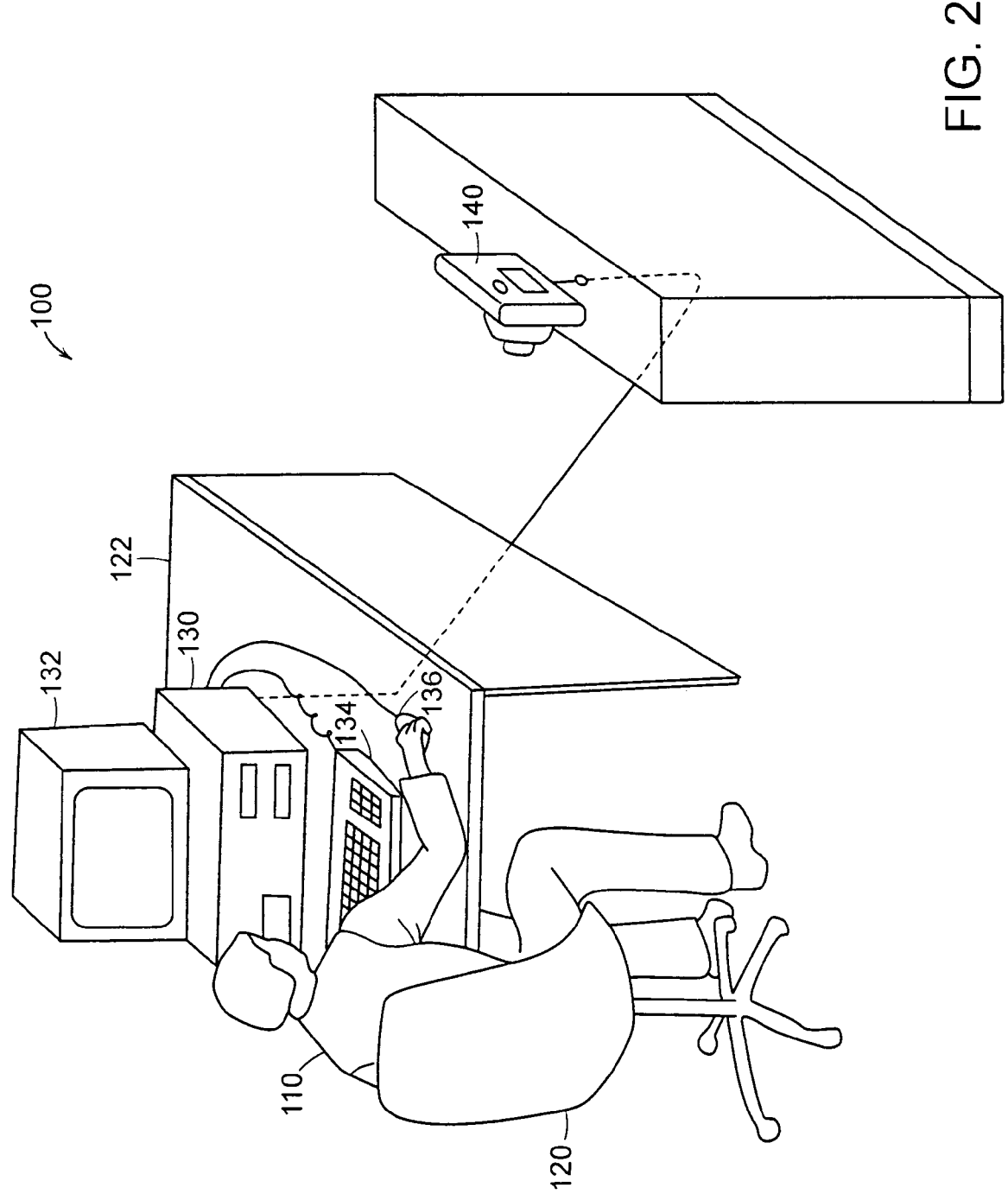
FIG. 2 is a schematic view of a tracking system during keyboarding activities.

FIG. 2 shows an ergonomic tracking system 100 that is used in one embodiment, to help a user 110 to have correct posture during keyboarding activities. In general, a camera 140 observes a user's 110 physical environment, such as the user entering information at a computer station or input area. The computer station or input area may include, alone or in combination, a chair 120, a work surface 122, a central processing unit 130, a display monitor 132, a keyboard 134, a mouse 136, or other devices. Other devices can be for example, a keypad, a joystick, a trackball, a touchpad, a wand, a touchscreen, a printer or any other known input or output device. Based on the user's 110 physical environment, the system 100 determines the user's 110 posture and outputs to the user 110 an indication of the user's posture relative to a target correct posture.

In a particular embodiment, the user 110 at the keyboard 134 or other input device is viewed using one camera 140. Digital images generated by the camera 140 or associated third party image software are processed by the system 100 to detect the body, the keyboard 134 (or other input device), the display monitor 132 and other aspects of the user environment, in each frame. In one embodiment, the system 100 or camera 140 can upload the digital images to the Internet for viewing or further processing. The camera can also be an embedded camera (e.g. in computer 130, cell phone or other device). It should be understood that the system 100 may be implemented with multiple cameras 140.

Figure 3:
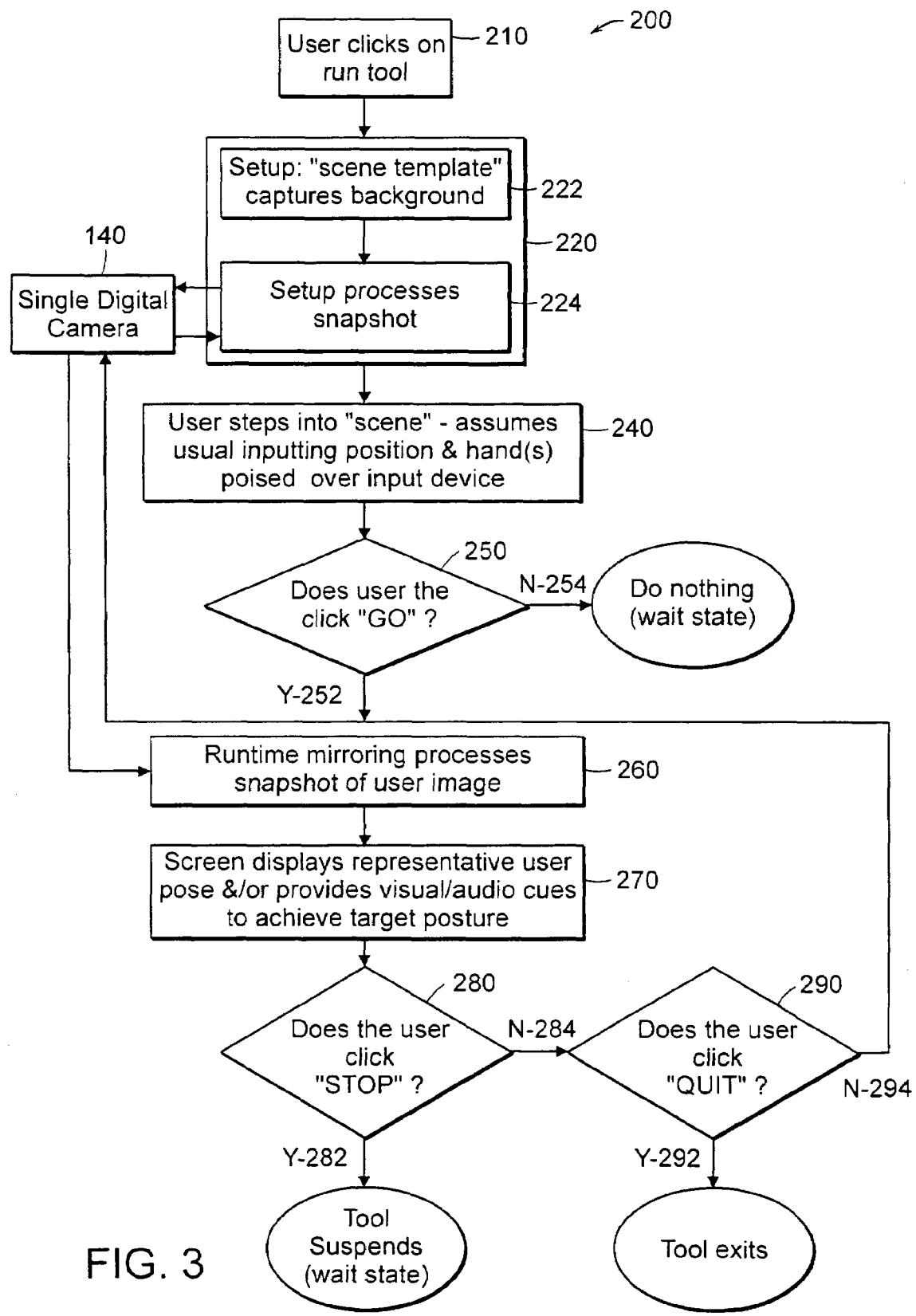
FIG. 3 is a flow diagram of the present invention.

FIG. 3 shows a flow diagram 200 of an implementation of the ergonomic tracking system 100 of FIG. 2. In one embodiment, the system 100 includes an initialization module 210, a setup module 220, an active scene module 240, a first determination module 250, a runtime mirror module 260, a display module 270, a second determination module 280, and a third determination module 290.

Initialization Module (210) allows the user 110 to initialize or "start" the ergonomic tracking system 100 of FIG. 2. This can be accomplished by the user 110 "clicking" or otherwise selecting an icon on the monitor 132 screen view using the mouse 136 or other input device. The icon activates the ergonomic tracking system 100.

The setup module 220 includes a scene template module 222 and a snapshot module 224. The scene template module 222 and the snapshot module 224 capture the background of the user's environment without the user being present in the scene. The physical environment can include (a) the keyboard 134 and/or other input device(s); (b) the viewing screen/monitor/embedded display 132; (c) the chair 120, a desk/pedestal/other supporting furniture 122; and (d) any other elements in the physical environment. The system 100 takes an initial picture or snapshot with digital camera 140. The camera 140 can be either operated automatically via electronic self-timer, "movie mode" or other existing camera means, or by a third party. The setup module 220 uses resulting digital image from the camera 140 to form the initial background scene of the user's environment. In one embodiment, the setup module only needs to be run once unless the environment materially changes, e.g. the furniture was reconfigured.

The active scene module 240 allows the user 110 to physically enter the "scene" and assumes his/her generally working (inputting) position. For example, the user 110 can sit at the computer station and position his/her hands over the keyboard 134 or the mouse 136 of FIG. 2.

Intermediate human representation is comprised of an angled vector space and/or other internal data model. The active scene module 240 anticipates successive tracking in nearby representational space. As such, modeling of the user 110 and session-level information may be stored for this user. Application-level information may be stored for a user, company (or a home environment). Further, modeling information can be sent (anonymously) to a central repository such that modeling can be improved for subsequent users.

The first determination module 250 allows the user 110 to decide whether to start tracking (252) or remain in a "wait state" (254). If the user 110 decides to start tracking (252), the user 110 clicks an icon on the monitor 132 screen view using the mouse 136 or other input means. Once viewing has started, the system 200 takes a snapshot of the "scene" with the user 110 present using the digital camera 140.

To model the user's body at the keyboard 134 or other input device, the digital images from the camera 140 are processed to detect the user 110 in the physical environment and retain an intermediate representation of the user 110 for successive image processing and display processing. For example, an approximate profile view may be sufficient for obtaining a representative pose.

As shown with reference to FIG. 2, ergonomic positions generally involve as much body bilateral symmetry as feasible. Further, using an input device commonly involves activation of large muscles (e.g. spinal, arms, legs) and fine hand/finger muscles, with upper limbs ergonomically proximate to the body. Therefore, sufficient pose information can be gleaned from 2-D digital images. However, although a single camera 140 is used in keeping costs low, there may be occasions where one camera view does not yield sufficient information. As such, multiple cameras 140 providing multiple camera views may be used to produce for example a frontal profile and/or an oblique view.

The runtime mirror module 260 processes the snapshot of the user's 110 image. The processed snapshot yields/derives a representation of the user's 110 posture (position) in the scene. Multiple independent detector, segmenter, estimator, and/or classifier modules can be used to achieve accuracy in real-time with low error rates. As the user 110 inevitably changes working (input) position the user's 110 movements are tracked by runtime mirror module 260. Mirroring reflects such physical changes to the positions of the user's 110 various body parts. Mirroring includes both body modeling and body tracking.

Mirroring of the user's 110 body at the keyboard 134 or other input device occurs in real-time. Thus, tracking of large user movements and/or fine user movements keeps pace over time. For example, large movements such as standing up or sitting down can involve shifting from one major ergonomically-sanctioned position to another.

The display module 270 outputs the processed snapshot to the user 110 in a screen view rendered or otherwise displayed on the monitor 132 in an application window. The application window can be one of multiple windows running in a windowing system (such as Microsoft Windows).

In one embodiment, the screen view includes the user's image in the environment of the scene (i.e. current position), superimposed by or otherwise in respect to a target correct posture indication. The target correct posture indication may be produced by line art, graphics, shading techniques (with or without the user's image), and the like. The system 200 may also provide visual and/or audio cues to help the user 110 achieve a correct target posture.

Use of the display module 270 allows a user 110 to learn/train from his/her previous activity. As for many kinds of physical activity, the user 110 learns to correctly position his/her body parts using such physical modeling. Both negative modeling (incorrect pose) and positive modeling (target pose or "how-to-get-to" target pose) contribute to the physicality of user 110 learning, such that "muscle memory" engages. If a pose is incorrect, visual and/or audio cues signal the user 110. These visual and/or audio cues can be a graphic highlight/color, an audio signal, a flashing signal, and/or other visual and audio effects known.

In some embodiments, viewing may be used more than training. For example, depending upon the level of a user's 110 health and corporate policy, a user 110 may opt to run viewing in the windowing foreground at select points during the day or simply in the background all day long.

The second and third determination modules 280, 290 allow the user 110 to determine whether to suspend viewing (282), continue viewing (284, 294) or quit the system (292). If the user 110 decides to continue viewing (284, 294), the system 200 takes another snapshot of the "scene" at 252, and repeats modules 260, 270, 280 and 290 until the user 110 decides to quit (292) or suspend (282) the system 100.

Figure 4:
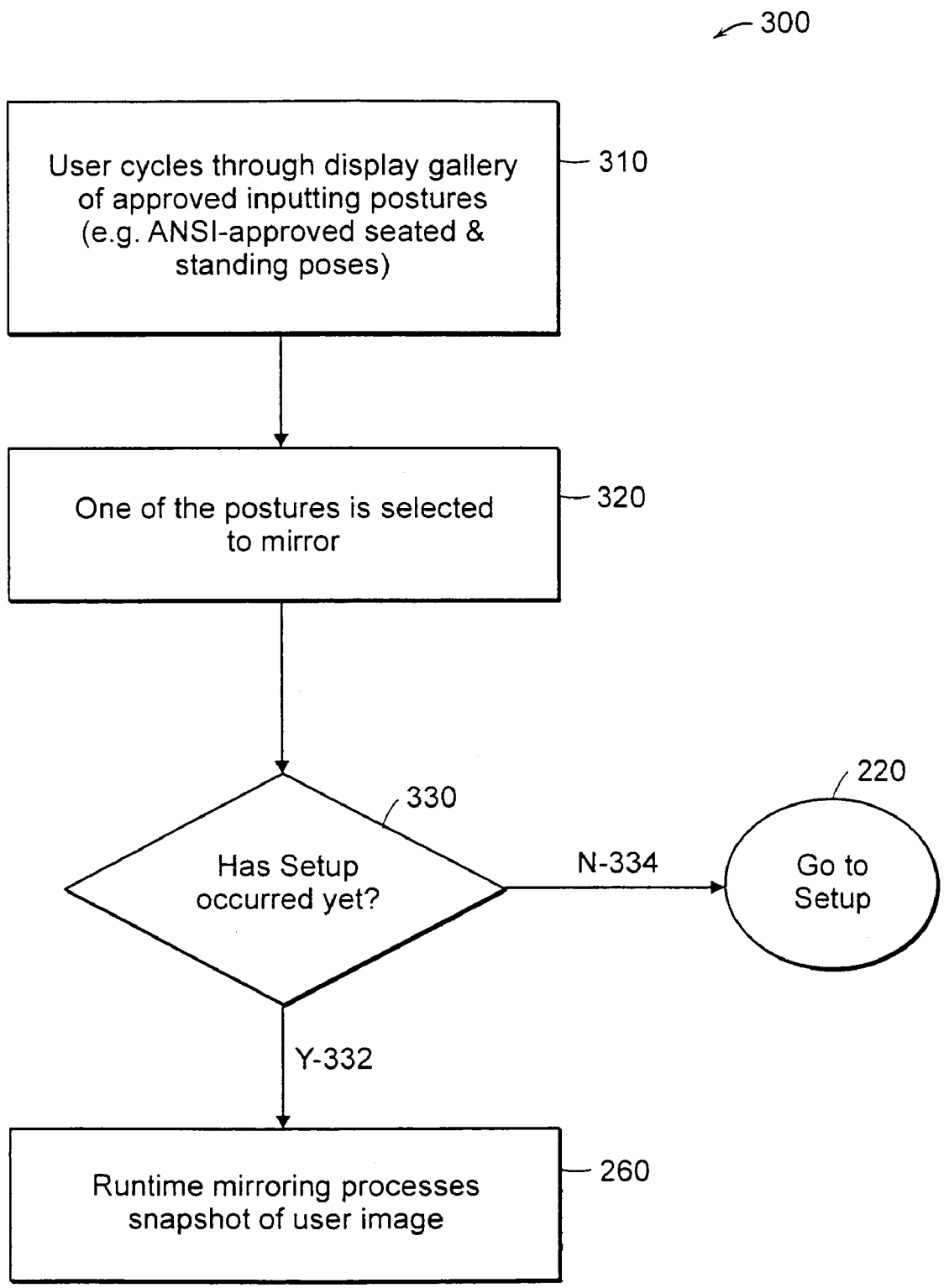
FIG. 4 is a flow diagram of an optional process in addition to the flow diagram described in FIG. 3.

FIG. 4 shows a flow diagram 300 of an optional training process in addition to the flow diagram described in FIG. 3. In another embodiment, the system 100 (FIG. 2) can include a display gallery module 310, a mirror selection module 320, and a setup determination module 330.

The display gallery module 310 allows user 110 (FIG. 2) to cycle through a display of working postures. For example, ANSI-approved seating and standing poses. These serve as candidate target correct postures for various poses.

The mirror selection module 320 allows the user 110 to select one of the working postures provided by the display in 310. The chosen working posture is compared to the user's 110 actual (camera 140 imaged) posture.

The setup determination module 330 prompts the user 110 whether the setup module 220 (FIG. 3) has been completed. If the setup module 220 has been completed (332), the system 300 proceeds with the runtime mirroring module 260 described above in FIG. 2. If the setup module 220 has not been completed (334), the system 300 proceeds to the setup module 220.

The present invention provides a low cost mechanism for preventing various kinds of incapacitating repetitive trauma that occur through incorrect ergonomic usage. The present invention uses real-time mirroring and positive modeling to address both prevention and therapeutic purposes.

Figure 5A:
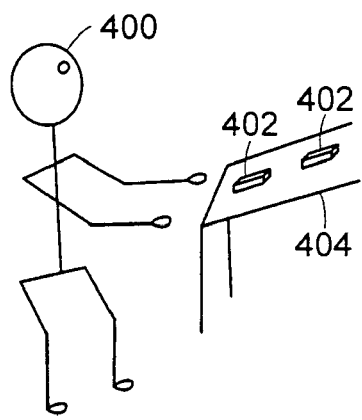
FIGS. 5A-5C illustrate a user in a repetitive motion-type environment.
Figure 5B:
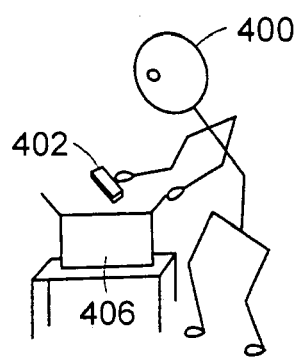
Figure 5C:
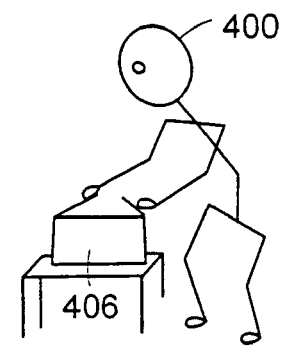

FIGS. 5A-5C illustrate a user in a repetitive motion-type environment. The user 400 reaches for items 402 coming off a conveyer belt 404. The user 400 then places the items 402 in a packaging container 406. Once the user 400 fills the packaging container with items 402, the user 400 closes the packaging container 406. The embodiments of the present invention can be used to provide the user 400 with correct body positioning information with relation to this type of repetitive motion (i.e. throughout the series of body positions forming the repetitive motion). As such, traumas such as lower back injury may be avoided.

Other embodiments of the invention can be used for keyboarding, gaming, keypadding and the like. Keyboard users commonly input via a variety of alternative keyboards and pointing devices, generally while viewing on a (screen) monitor associated with a computer, web TV or networked system such as the Internet. Use of other keyboards however may be included, such as PDAs, handheld electronic devices, portable phones, or text messaging systems, etc. Gaming users input via a variety of keyboards and/or embedded joysticks, triggers, or trackballs, generally while viewing on a (screen) monitor associated with a computer, web TV or networked system such as the Internet. For gaming users, an automated tool as above allows assessment of whether they are "doing it right" (maintaining a proper position throughout), while joysticking, trackballing or typing. Users of keypads such as the Blackberry or vertical market devices, can view this invention on a screen/monitor associated with a computer, web TV or networked system such as the Internet.

While this invention has been particularly shown and described with references to preferred embodiments thereof, it will be understood by those skilled in the art that various changes in form and details may be made therein without departing from the scope of the invention encompassed by the appended claims.

What is claimed is:

1. A computer system for providing real-time feedback about a user's posture, comprising:
    an environmental module for determining a subject physical environment;
    a biomechanical module for determining at least a portion of a user's posture in the determined subject physical environment; and
    an output module for providing to the user a real-time indication of the determined user's posture relative to a target correct posture associated with the determined subject physical environment, the target correct posture being in accord with a standardized posture for the determined subject physical environment.

2. The system of claim 1, wherein the standardized posture is an American National Standards Institute (ANSI) standard.

3. The system of claim 1, wherein the standardized posture is a published standard.

4. The system of claim 1, wherein the standardized posture is an industry standard.

5. A computer system for providing real-time feedback about a user's posture, comprising:
- an environmental module for determining a subject physical environment of the user;
- a biomechanical module for determining at least a portion of a user's posture in the determined subject physical environment, the portion of a user's posture including a body portion controlled by at least one of small muscles and large muscles; and
- an output module for providing to the user a real-time indication of the determined user's posture relative to a target correct posture associated with the determined subject physical environment.

6. The computer system of claim 5, wherein the body portion controlled by at least one of small muscles and large muscles includes at least one of: a torso; a hand area; a neck; an arm area; and a leg area.

7. A computer system for providing real-time feedback about a user's posture, comprising:
- an environmental module for determining a subject physical environment;
- a biomechanical module for determining at least a portion of a user's posture in the determined subject physical environment; and
- an output module for providing to the user a real-time indication of the determined user's posture relative to a target correct posture associated with the determined subject physical environment, the user's posture being one of a seated posture, a standing posture, a reaching posture, and a manipulating posture.

8. The computer system of claim 7 wherein the biomechanical module further determines at least a portion of a user's posture when transitioning from a first posture to a subsequent posture; and
- wherein the output module further provides a real-time indication of the determined user's transition relative to a target transition from the first posture to the subsequent posture.

9. The computer system of claim 7 wherein the user's posture is static.

10. A method for providing real-time feedback about a user's posture, comprising computer implemented steps of:
- determining a subject physical environment;
- determining at least a portion of a user's posture based on the determined subject physical environment; and
- providing to the user a real-time indication of the determined user's posture relative to a target correct posture associated with the determined subject physical environment, the target correct posture being in accord with a standardized posture for the determined subject physical environment.

11. The method of claim 10 wherein the standardized posture is an American National Standards Institute (ANSI) standard.

12. The method of claim 10, wherein the standardized posture is a published standard.

13. The method of claim 10, wherein the standardized posture is an industry standard.

14. A method for providing real-time feedback about a user's posture, comprising computer implemented steps of:
- determining a subject physical environment;
- determining at least a portion of a user's posture based on the determined subject physical environment, the portion of a user's posture including a body portion controlled by at least one of small muscles and large muscles; and
- providing to the user a real-time indication of the determined user's posture relative to a target correct posture associated with the determined subject physical environment.

15. The method of claim 14, wherein the body portion controlled by at least one of small muscles and large muscles includes at least one of: a torso; a hand area; a neck; an arm area; and a leg area.

16. A method for providing real-time feedback about a user's posture, comprising computer implemented steps of:
- determining a subject physical environment;
- determining at least a portion of a user's posture based on the subject physical environment; and
- providing to the user a real-time indication of the determined user's posture relative to a target correct posture associated with the determined subject physical environment, the user's posture being one of a seated posture, a standing posture, a reaching posture, and a manipulating posture.

17. The method of claim 16 wherein the step of determining at least a portion of the user's posture in the determined subject physical environment further includes determining at least a portion of a user's posture when transitioning from a first posture to a subsequent posture; and
- wherein the step of providing to the user a real-time indication of the determined user's posture relative to a target correct posture associated with the determined subject physical environment further includes providing a real-time indication of the determined user's transition relative to a target transition from the first posture to the subsequent posture.

18. The computer system of claim 16 wherein the user's posture is static.

* * * * *